United States Patent [19]

Jewett

[11] 4,417,586
[45] Nov. 29, 1983

[54] BLOOD PRESSURE MEASURING DEVICE

[75] Inventor: Warren R. Jewett, Tucson, Ariz.

[73] Assignee: Vit Vet Research Group, Inc., Marion, Ind.

[21] Appl. No.: 235,569

[22] Filed: Feb. 18, 1981

Related U.S. Application Data

[62] Division of Ser. No. 905,795, May 15, 1978, Pat. No. 4,290,434.

[51] Int. Cl.³ .............................................. A61B 5/02
[52] U.S. Cl. .................................... 128/680; 128/685
[58] Field of Search .............................. 128/680–683, 128/685

[56] References Cited

U.S. PATENT DOCUMENTS 4,112,929  9/1978  Affeldt et al. ..................... 128/680

OTHER PUBLICATIONS

Watanabe, S. et al., "New Electronic Sphyg Lets Patients Monitor Their BP Unassisted", JEE No. 107, pp. 12-16, Oct. 1975.

*Primary Examiner*—Kyle L. Howell
*Assistant Examiner*—Francis J. Jaworski
*Attorney, Agent, or Firm*—Woodard, Weikart, Emhardt & Naughton

[57] ABSTRACT

A noninvasive blood pressure measuring device includes display means which may be digital readouts, a sphygmomanometer or other similar means, a compression cuff, a first flexible tube, a second flexible tube, an air leak valve and monitoring, control and display circuitry. Within the compression cuff is an inflatable bladder which extends in a longitudinal direction for substantially the entire length of the compression cuff. The monitoring, control and display circuitry includes a piezoelectric crystal assembly which provides electrical signals in response to air pressure levels and changes within the first flexible tube. The first tube connects this piezoelectric crystal assembly with the compression cuff and the second tube has a hand pump at one end for inflating the bladder. The air leak valve is in line with the first tube and the air leak valve has a continuously open air escape aperture of a size which corresponds to a predetermined leak rate proportional to the pressure in the bladder. When a sphygmomanometer is incorporated as part of the display means, a branch tube connects the first flexible tube to the sphygmomanometer and a pair of light-emitting diodes mounted to the dial face of the sphygmomanometer indicate when sphygmomanometer readings should be taken for systolic and diastolic conditions. When digital readouts and a microprocessor are used as part of the monitoring, control and display circuitry, data such as, for example, heart rate and mean pressure in addition to systolic and diastolic pressures are automatically presented and may be read directly.

9 Claims, 16 Drawing Figures

BLOOD PRESSURE MEASURING DEVICE

This application is a division, of application Ser. No. 905,795, filed May 15, 1978 now U.S. Pat. No. 4,290,434.

BACKGROUND OF THE INVENTION

This invention relates in general to blood pressure measuring devices and in particular to such devices which are automatic and do not require a stethoscope for identifying systolic and diastolic conditions and which may also provide mean pressure and heart rate in a direct reading manner.

Blood pressure measurement as a medical procedure is not new nor are the basic concepts or equipment which are employed new. Conventional measurement procedures require that a compression cuff be snugly wrapped around the patient's right arm approximately one inch above the antecubital fossa location. The compression cuff includes an inflatable bladder at one end and this bladder must be applied directly over the artery with the remainder of the compression cuff being used as a wrap to secure the bladder in place. The compression cuff (actually the inflatable bladder) is inflated rapidly to a pressure above the assumed or previously determined systolic pressure. By means of a manually released valve, the cuff is deflated at a rate of two to three millimeters (mm) of mercury (Hg) per heartbeat. With the bell of a stethoscope placed snugly over the artery (thereby producing an airtight seal) the physician may either watch an aneroid dial or column of Hg of a suitable sphygmomanometer and note the pressure at which characteristic changes in the Korotkoff sounds occur. From these sounds, created by pressure controlled compression waves, the systolic and diastolic blood pressures can be determined.

This conventional method has various shortcomings in terms of convenience, versatility and accuracy. It is necessary for the physician or medical personnel taking the blood pressure to accurately position the inflatable bladder over the artery, to make an air tight seal with the bell of a stethoscope over the artery, to manually control the pressure release rate and to attempt to read the corresponding pressure when particular characteristic sounds are detected through the stethoscope.

In an attempt to improve blood pressure measuring techniques, certain modifications have been made to conventional blood pressure measuring equipment. Examples of some of these modifications are shown by the following patents:

| Patent No. | Patentee | Issue Date |
| --- | --- | --- |
| 3,651,798 | Egli et al. | 3/28/72 |
| 3,993,047 | Peek | 11/23/76 |
| 4,005,701 | Aisenberg et al. | 2/01/77 |

Egli et al. discloses an electronic blood pressure indicator for use with conventional blood pressure measuring equipment. This device includes a microphone for translation of arterial blood flow sounds into electrical signals. The electronics are somewhat complicated due to the need to filter out undesired and extraneous frequencies, and to distinguish the characteristic changes in the Korotkoff sounds.

Peek discloses a type of electronic blood monitoring device which is used to monitor blood circulation conditions. This device includes an infared radiation source and a corresponding sensor which are placed in contact with the skin of the subject. This device is not related to conventional sphygmomanometers nor is it usable for reading blood pressure.

The patent to Aisenberg et al. discloses a noise-rejecting electronic sphygmomanometer which utilizes two microphones positioned adjacent the inflatable bladder in a conventional compression cuff. The first microphone is used to pick up Korotkoff sounds as the cuff is deflated and blood flow in the patient's arm resumes. The second microphone is used to pick up background noises so that electronic circuit discrimination and signal comparisons can be used to provide an accurate sound indication which is unaffected by such background noises.

With each of the aforementioned devices there are numerous shortcomings which exist. To begin with, all presently available blood pressure measuring devices require the accurate placement of the bladder directly over the artery (this is true even with the use of microphones in lieu of a stethoscope). Secondly, known electronic blood pressure measuring devices rely entirely on pickup of the characteristic changes in Korotkoff (pressure wave) sounds and thus employ conventional microphones. The need to filter and isolate the correct sounds results in relatively complex and thus costly circuitry. Furthermore, the number of circuit components required is large and this has an effect on labor costs and system reliability. A third shortcoming is that each device is designed for only taking the blood pressure of humans and for using, for example, the left arm of the patient for the measurement. It is a recognized rule that in order to obtain an accurate reading, the width of the inflatable bladder should be approximately 20% greater than the diameter of the limb on which it is used. Therefore, it would be an advantage if blood pressure devices could be provided with detachable and interchangeable cuffs so that the blood pressure of different sizes of patients, and especially infants, could be accurately measured by using a single measurement unit, such as a sphygmomanometer, but with different, interchangeable, compression cuffs. Another shortcoming with conventional devices is that a portion of the medical personnel's attention is taken up with the activity of manually releasing the pressure from the bladder and attempting to do so at a regular rate, such as 2-3 mm of Hg per second. Automatic air pressure release means would permit the medical personnel to devote their full attention to hearing and noting the corresponding pressure at systolic and diastolic conditions and the monitoring of a dial to make such determinations.

A further shortcoming of such present-day devices involves the fact that these conventional devices are only usable on human beings and are not acceptable for animals due to the differences in anatomy between such animals and human beings. For example, in dogs, the arteries within the animal's limbs are somewhat recessed and a conventional cuff and bladder applies pressure to only one side of the limb and will act to push the artery back and away from the surface of the limb where the stethoscope bell is normally placed. The surface of the artery will thus not be in close proximity to the bladder portion of the cuff as is required for accurate readings. A further difficulty with animals, such as dogs, is that the animal's artery in an appendage, such as a hind leg, may be somewhat randomly positioned and thus may be difficult to locate and the requisite precise placement of the stethoscope bell over the artery may not be possible. In addition, when the size of the animal's appendage is small, there may not be sufficient surface skin area to permit the bell of the stethoscope to make a seal over the artery and due to the fact that the edges of the stethoscope overhang the sides of the appendage, the accuracy of any readings taken will be subject to noticeable error. Therefore, arterial catheterization—a method which is both lengthy and complicated—must be used on animals in order to accurately measure their blood pressure.

Although only two classes of subjects have heretofore been mentioned, human beings and animals, a third class exists. This class includes infants whose physical size requires a specially sized compression cuff and whose artery size and position make conventional devices unreliable. Infants' arteries are so small, such as the brachial artery which is often used, that they are difficult to find and when a stethoscope must be used (as with conventional blood pressure measuring devices) positioning variations can cause a 10 to 20 percent difference in the readings. Also, as previously mentioned, there may not be adequate skin area over the artery for the bell of the stethoscope to make an air-tight seal. Consequently when an infants' condition is being monitored, there is no way to tell if blood pressure variations are due to the measuring equipment and technique or due to a physical change in the infant. This problem can be eliminated by providing measurement means which does not require a stethoscope or the precise positioning of pick-up microphones. It would also be an improvement to such devices if other useful data could be obtained at the same time blood pressure readings are taken, and displayed in a conveniently readable manner, without having to subject the patient to further medical procedures or testing.

SUMMARY OF THE INVENTION

A blood pressure measuring device according to one embodiment of the present invention comprises a sphygmomanometer, a compression cuff having an inflatable bladder therein, a flexible tube, means for inflating the inflatable bladder and an air leak valve having a continuously open air escape aperture therein sized for a predetermined leak rate. The flexible tube is connected between the inflatable bladder and the sphygmomanometer and the air leak valve is coupled to and coaxial with this tube.

A diagnostic device for determining characteristics of a blood circulation system according to another embodiment of the present invention comprises means for applying artery occluding pressure to an appendage artery, means for gradually releasing the occluding pressure, means for sensing the pressure of blood pulsating in the artery, means for indicating pressure changes occurring in the artery and means for determining and displaying systolic blood pressure, diastolic blood pressure, heart rate and mean blood pressure.

One object of the present invention is to provide an improved blood pressure measuring device which is equally well-suited for use on adults, infants and animals.

Another object of the present invention is to provide a blood pressure measuring device which is virtually fully automatic with the only manual activities being the wrapping of the compression cuff and the inflating of the bladder.

Yet another object of the present invention is to provide an electronic indicator circuit which utilizes pressure changes in lieu of sounds in order to detect systolic and diastolic conditions.

Related objects and advantages of the present invention will be apparent from the following description.

DESCRIPTION OF THE PREFERRED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figures 1, 2:
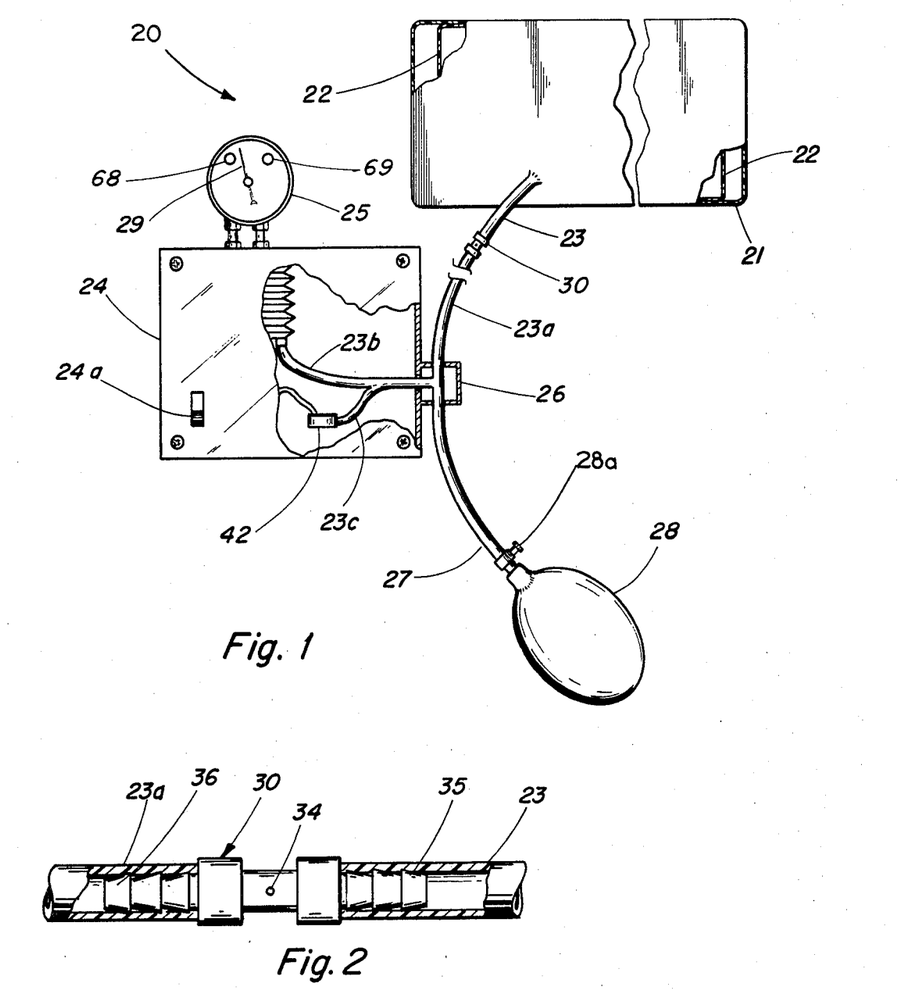
FIG. 1 is a perspective view of a blood pressure measuring device according to a typical embodiment of the present invention.
FIG. 2 is a perspective view of an air leak valve comprising a portion of the FIG. 1 device.

Referring to FIG. 1, there is illustrated a blood pressure measuring device 20 according to the present invention. Device 20 includes compression cuff 21 with inflatable bladder 22 therein, first flexible tube 23, control unit 24, dial indicator 25, junction 26, second flexible tube 27 and bulb 28. The general appearance of device 20 is that of a conventional sphygmomanometer device for measuring a person's blood pressure. However, there are important distinctions which will be discussed hereinafter. The particular manometer shown is that of an aneroid manometer which consists of a metal bellows, the inside of which is connected to the compression cuff. Variations of pressure within the system cause the bellows to expand and collapse and this movement rotates a gear that turns needle 29 to make the indicated dial reading. Device 20 is equally suited for use with a mercury-gravity manometer and although such a device is not shown, it is to be understood that the principles and features discussed herein are equally applicable. Control unit 24 houses a control circuit, described hereinafter, which is energized by means of ON-OFF switch 24a.

Although the exterior appearance of compression cuff 21 is much like that of a conventional compression cuff as is well known to the blood pressure measuring art, the internal design of compression cuff 21 is unique. Flexible tube 23 connects to and opens into inflatable bladder 22 and this bladder extends longitudinally for substantially the entire length of compression cuff 21. This elongated condition of inflatable bladder 22, which is significantly different than conventional bladders, permits the entire bladder 22 to be wrapped around the portion of anatomy which is being used for the blood pressure measurement. Conventional inflatable bladders are constructed of an elastomeric compound which provides sufficient expansion to accommodate the air pumped into the bladder. Due to the increased size of bladder 22, the degree of elasticity may be less and vinyl material is suitable. The result is that pressure is applied radially inward to that portion of anatomy from all sides in a uniform circumferential manner. Although the flow of blood will be restricted by this type of design in much the same manner as a conventional compression cuff restricts the flow of blood, the unique distinction is that when using the described device on animals such as, for example, dogs, the artery involved will not be pushed back and away from the bladder into a recessed location. Thus an artery of such an animal which may normally be in a recess or depression can be used for accurate blood pressure measurement due to the fact that this type of compression cuff will virtually hold the artery in its normal position and the bladder will be placed in close proximity to this artery as the bladder is inflated.

Bulb 28, which acts as a hand pump, is used as the means to inflate bladder 22. As the attending medical personnel squeezes on bulb 28, air will be introduced into bladder 22 and at the same time the corresponding pressure will be indicated by means of needle 29 on dial indicator 25. Junction 26 serves as a connector between flexible tube 27, flexible tube 23 (23a) and tubes 23b and 23c which enter control unit 24 and connect to the aneroid manometer. With conventional blood pressure measuring devices, there would be a small manually operated valve adjacent bulb 28 within tube 27 which would allow air to be released from bladder 22 thereby lowering the system pressure. In lieu of this manually operated conventional device, there is included with the present system an air leak valve 30. Once bulb 28 has been used to rapidly inflate bladder 22 to a pressure level somewhat above the presumed systolic condition, valve 30 which has a continuously open aperture 34, releases the air from bladder 22 at a predetermined rate. Aperture 34 is intermediate the ends of valve 30 and the air release flow rate is dependent on the pressure within bladder 22, this rate gradually decreasing over the time interval between systolic and diastolic conditions. A manual valve 28a for rapid deflation is also provided.

Although mention has been made of the fact that device 20 is usable on animals for measuring their blood pressure, due to the design of compression cuff 21 and inflatable bladder 22, it is to be noted that device 20 is equally applicable to adults, children and infants. It is a recognized rule that in order to obtain an accurate reading, the width of the inflatable bladder 22 should be approximately 20% greater than the diameter of the limb around which the compression cuff 21 is wrapped. Therefore, a single size of compression cuff 21 and inflatable bladder 22 would not be usable for all classes and sizes of patients. In order that the control unit 24 and the corresponding sphygmomanometer which is used with control unit 24 do not have to be unnecessarily duplicated, device 20 is provided with means by which compression cuff 21, inflatable bladder 22 and flexible tube 23 can be removed and a differently sized compression cuff attached. This detachable compression cuff feature is provided by means of air leak valve 30 which is tapered on each end and extends outwardly in order to accommodate main tube 23 on one end and a smaller branch tube 23a on the opposite end. Referring to FIG. 2, it is shown that tubes 23 and 23a are merely pressed over the ends 35 and 36 respectively of air leak valve 30. Suitable surface deforming may be provided on ends 35 and 36 such as knurling, ridges or lips in order to securely hold tubes 23 and 23a in position while still permitting the quick and easy disconnect of these tubes. The region surrounding aperture 34 may be recessed in order to keep foreign matter from clogging aperture 34 and for preventing aperture 34 from resting against a surface which might restrict the air leak flow. As will be described hereinafter, it is also possible to replace air leak valve 30 with a new valve having a differently sized aperture 34 in order to vary the air leak rate. Thus air leak valve 30 may either be detached with compression cuff 21 and tube 23 by disconnecting at end 36, or air leak valve 30 may remain with the basic unit and compression cuff 21 and tube 23 by disconnecting at end 35.

Figure 3:
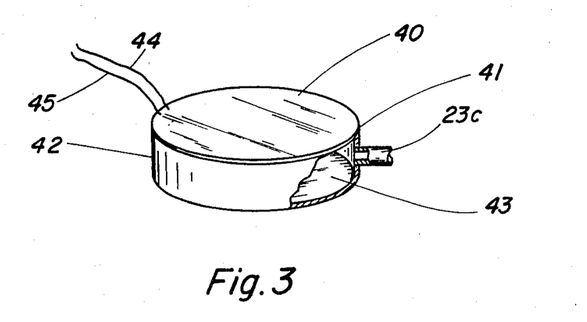
FIG. 3 is a perspective view of a piezoelectric crystal apparatus comprising a portion of the FIG. 1 device.

The conventional method of taking a blood pressure measurement is to apply a compression cuff around the limb of the patient, restrict the blood flow, gradually release the pressure and as the pressure decreases and blood flow resumes listen by way of a stethoscope to Korotkoff sounds which, to the trained ear, are indicative of systolic and diastolic conditions. Even newer electronic blood pressure measuring devices still rely on using these sounds in order to determine systolic and diastolic conditions. The present device employs a piezoelectric crystal 40 within control unit 24 as part of the control and display circuitry. Leading from junction 26 within control unit 24 are two additional sections of tubes, 23b which leads to the sphygmomanometer, and 23c which leads to piezoelectric crystal apparatus 41. Apparatus 41 includes crystal 40 which is sealed around its periphery and mounted atop housing 42 which has a hollow cavity 43 therein. Tube 23c opens into cavity 43 and as pulsed variations in pressure are delivered through tubes 23, 23a and 23c, piezoelectric crystal 40 flexes and undergoes stress variations which are converted into electrical signals and delivered to the control and indicating circuitry by means of wires 44 and 45 which are bonded to the surface of piezoelectric crystal 40.

Figure 4:
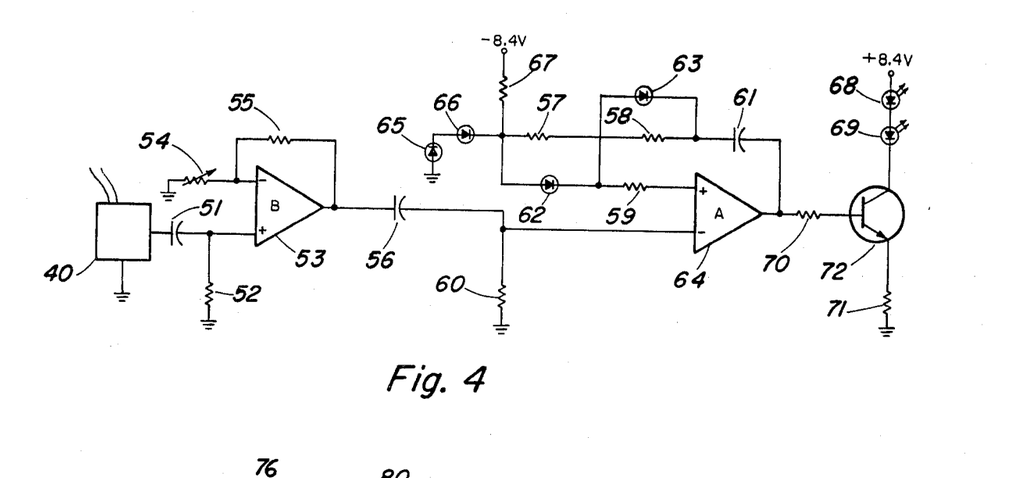
FIG. 4 is a schematic diagram of an indicator circuit comprising a portion of the FIG. 1 device.

Referring to FIG. 4, the signals out from the piezoelectric crystal 40 are introduced into a high pass RC filter comprising capacitor 51 and resistor 52 and from there into the positive input of one amplifier 53 of a dual operational amplifier, such as, for example, an LM 747 offered by Motorola Semiconductor Products, Tempe, Ariz., and which is used in a noninverting mode. Variable resistor 54 and feedback resistor 55 provide gain adjustment for this portion of the indicating control circuit and a minimum gain of 16 is selected. The output of amplifier 53 is AC coupled to the comparator-timing portion of circuit 50 by means of capacitor 56. The selected value of capacitor 56 is large enough so that amplified heart sounds are allowed to pass unattenuated. The comparator-timing portion of circuit 50 includes resistors 57, 58, 59 and 60, capacitor 61, diodes 62 and 63 and the remaining operational amplifier on the LM 747 integrated circuit chip, amplifier 64. A negative reference voltage is established by a series diode configuration including diodes 65 and 66, resistor 67 and a power supply potential of negative 8.4 volts. The pulse width is a function of resistors 57 and 58, capacitor 61, reference voltage and negative and positive saturation voltages of amplifier 64. The pressure fluctuations received by piezoelectric crystal 40 and which are converted and amplified by amplifier 53 will cause the comparator-timing portion of circuit 50 to illuminate light-emitting diodes 68 and 69 if the amplified signal out of amplifier 53 is greater than the selected reference voltage. The duration of illumination, approximately 0.25 seconds, is controlled by the selection of components and this duration is selected so that the illumination of the light-emitting diodes is easily visualized and yet does not conflict with rapid heartbeats which one might expect to occur over a variety of patients and circumstances.

Light-emitting diodes (LED's) 68 and 69 require approximately 0.015 amps in order to illuminate and the output portion of circuit 50 includes an output booster consisting of resistors 70 and 71 and transistor 72. A suitable component for transistor 72 is a 2N5172 offered by Motorola Semiconductor Products. The value of resistors 70 and 71 are analytically determined in order to deliver the necessary light-emitting diode current as well as to saturate transistor 72. Two mercury cell 8.4 volt batteries are used for the negative and positive power supply potentials. Although it is clear how the circuit just described can produce a current signal in response to a pressure change, the important feature of blood pressure measuring device 20 is how various pressure levels are detected so that the blood pressure at diastolic and systolic conditions can be identified.

Figure 5:
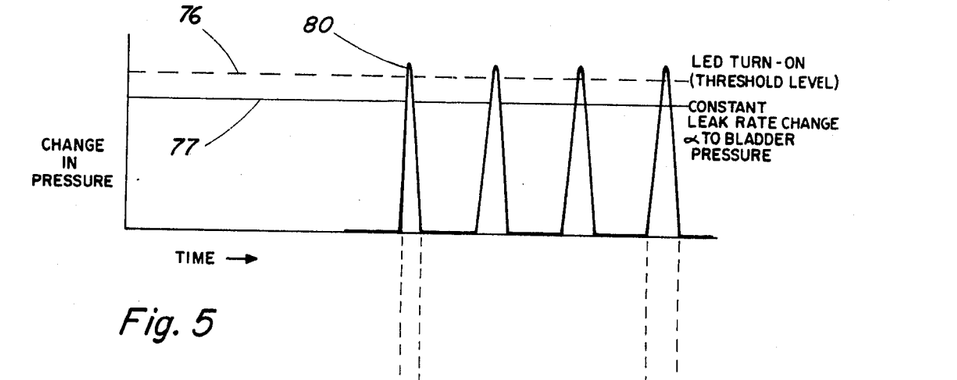
FIG. 5 is a graph of pressure change relative to time.
Figure 6:
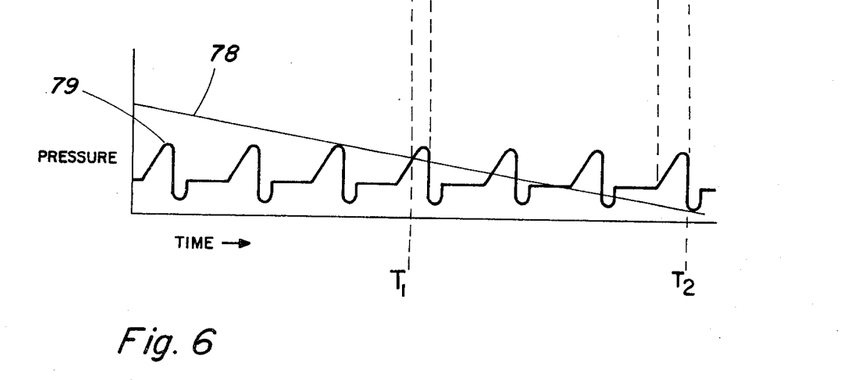
FIG. 6 is a graph of pressure relative to time.

Referring to FIGS. 5 and 6, there are illustrated two graphs which have the same horizontal (X) time axis and represent the interval during which a blood pressure measurement is taken. FIG. 5 has as its vertical (Y) axis scale, change in pressure as seen by piezoelectric crystal 40. An upper level indicated by line 76 must be exceeded in order to exceed the threshold or turn-on level for LED's 68 and 69. As the air within inflated bladder 22 escapes through opening 34 in air leak valve 30, the change in pressure will be relatively constant even though the actual pressure level is decreasing. This nearly constant pressure change indicated by line 77 is below the threshold level and the LED's remain off.

Referring now to the graph of FIG. 6, the vertical (Y) axis is tual pressure within tube 23 leading from bladder 22 to control unit 24. The decreasing bladder pressure is indicated by line 78 and the heartbeat of the subject is represented by repeating wave signal 79. When the pressure in bladder 22 exceeds the maximum pulsing pressure due to the subject's heartbeat, the blood flow will be temporarily occluded. As the pressure in bladder 22 is released through air leak valve 30, there will come a point in time ($T_1$) when the maximum heartbeat pressure first exceeds the occluding pressure of the bladder and blood begins to flow past the compression cuff. The flow of blood causes an increase in the circumference of the appendage at the location of the compression cuff and this size increase causes a pressure pulse in tube 23 which appears as spike 80 in FIG. 5. This spike corresponds to systolic condition and since spike 80 exceeds the turn-on level of line 76, LED's 68 and 69 will momentarily flash on. This initial flashing on signifies when dial indicator 25 should be read in order to obtain the systolic blood pressure measurement.

With subsequent heartbeats, additional spikes will occur causing LED's 68 and 69 to flash on and off. As the pressure in bladder 22 decreases even further there will occur a point in time ($T_2$) when the lowest pressure level of the heartbeat will exceed the occluding pressure and all the blood of each pulse will flow without causing any change in the appendage circumference. Consequently, there will not be any pressure spikes and the LED's will turn off and remain off until the measurement procedure is repeated.

Although device 20 has been discussed and described solely as a blood pressure measuring device, the indicating and control circuit 50 and other features of this device will permit basic modifications to be incorporated such as counting the rythymic beats with respect to a time interval and thereby determine the patient's heartbeat rate. In addition, it would be possible to convert dial indicator 25 to a digital readout means whereby the blood pressure at systolic and diastolic conditions could be numerically derived and presented as well as the mean pressure. As described in detail hereinafter, each of these various readings; heartbeat rate, systolic pressure, diastolic pressure and mean pressure can be individually and simultaneously displayed.

As has been previously described control unit 24 works in combination with dial indicator 25 to both indicate the pressure level within tube 23 and to flash OFF and ON light-emitting diodes 68 and 69 when the systolic pressure is present. Similarly, diastolic pressure is identified by taking the dial reading when the diodes turn off and remain off. In certain situations it may be desirable to obtain further information about a patient such as, for example, heart rate and mean blood pressure. Conventional manometers are not suitable for obtaining this type of blood circulation system data because these conventional manometers are designed solely for a single dial reading at any given instant of time, and such devices neither retain the data nor provide circuitry for obtaining other data.

Figure 7:
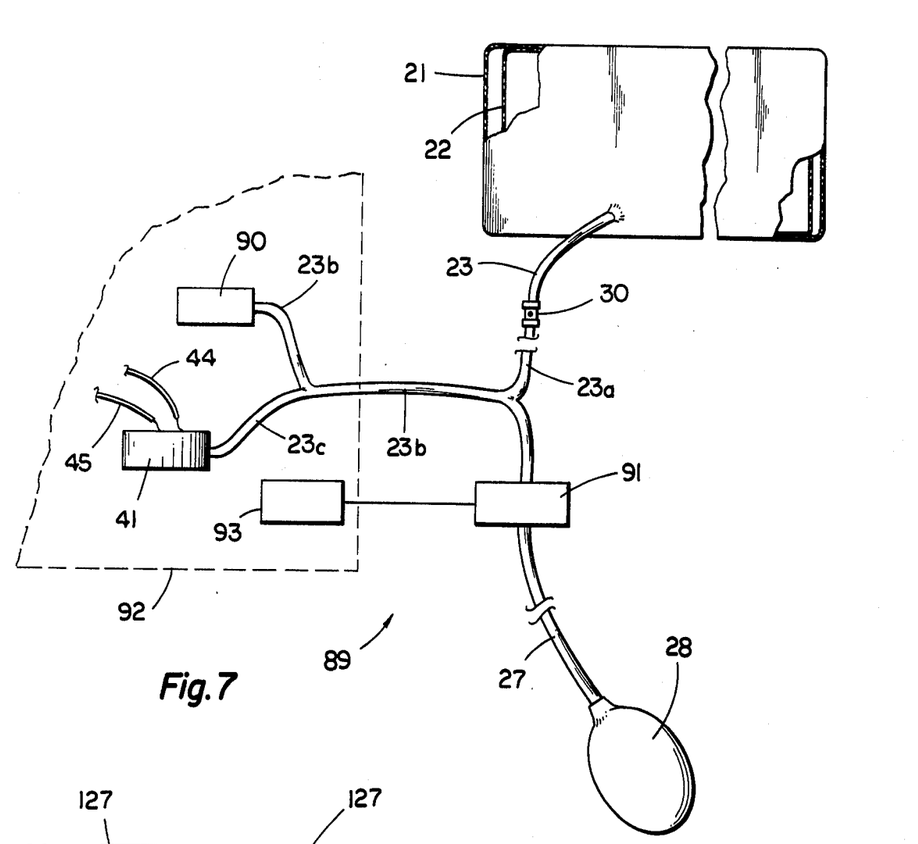
FIG. 7 is a diagrammatic view of a blood diagnostic device according to a typical embodiment of the present invention.

FIG. 7 illustrates an alternative blood pressure measuring device 89 which includes additional circuitry and additional capabilities over what has been previously described for device 20. Blood pressure measuring device 89 includes some of the same basic components used with device 20, such as, compression cuff 21, inflatable bladder 22, first flexible tube 23, second flexible tube 27, bulb 28, tubes 23a, 23b and 23c, air leak valve 30 and piezoelectric crystal apparatus 41. Additionally device 89 includes a pressure transducer device 90, solenoid air valve 91 and digital display console 92. Digital display console 92 houses the pressure transducer device 90, the piezoelectric crystal apparatus 41 and suitable analog and microprocessor circuitry for the operation of device 89 as will be further described hereinafter.

Figure 8:
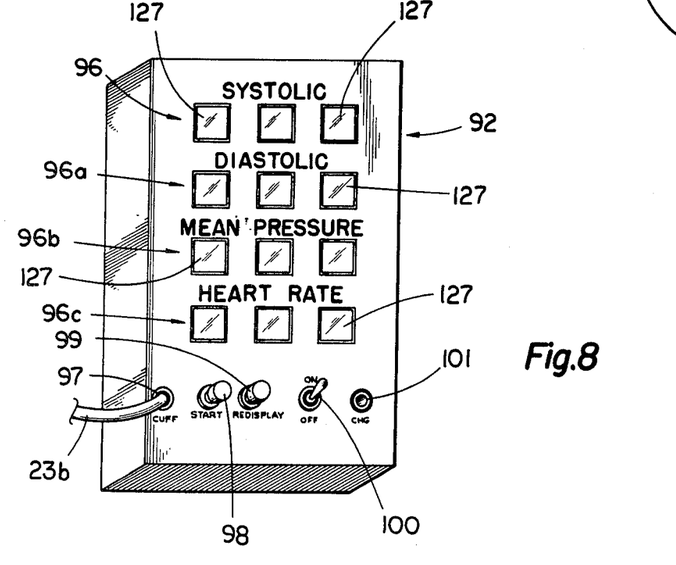
FIG. 8 is a perspective view of a digital display console comprising a portion of the FIG. 7 device.

Console 92 is illustrated in FIG. 8 and is diagrammatically represent by the broken lines in FIG. 7. Solenoid air valve 91 is located in line with flexible tube 27 and is powered by a D.C. to D.C. converter 93, also part of console 92, such that when energized, valve 91 connects the compression cuff 21 to the inflation bulb 28 by providing an open path through tube 27. Converter 93 is powered by a five volt battery 94 (see FIG. 10) and converter 93 provides outputs of plus and minus 15 volts. With initial turn on of device 89, solenoid air valve 91 is open to atmospheric pressure so that the pressure sensing components of device 89 may be automatically zeroed to the atmospheric pressure before blood pressure readings are taken. Once the diastolic blood pressure has been computed and displayed, the solenoid will hold that pressure for a predetermined interval of time and will then open in order to dump the pressure in the cuff and return the components to the atmospheric pressure level.

Digital display console 92 includes four display window groups 96, 96a, 96b and 96c each having three, seven-segment digital displays, a tube inlet port 97, a start switch 98, a redisplay buttom 99, ON-OFF switch 100 and a recharging input 101. Window group 96 is used to display the systolic blood pressure of the patient which is accurately computed by the monitoring, determining and display circuitry within console 92, and the direct reading capability of the digital displays eliminate the need to read a mechanically driven dial. Similarly, window group 96a displays the diastolic blood pressure, window group 96b displays the mean pressure of the patient and window 96c group displays the patient's heart rate. The mean pressure is derived from the systolic and diastolic blood pressure readings in accordance with the following expression:

$$P_M = P_D + \left(\frac{P_S - P_D}{3}\right)$$

where $P_M$ is the mean pressure, $P_D$ is the diastolic pressure and $P_S$ is the systolic pressure. Each of these readings is in terms of millimeters of mercury. Heart rate is derived by counting received heart beat pulses for 15 seconds and then multiplying the total number by 4 in order to express the heart rate in pulses per minute.

With the availability of blood circulation system characteristic data such as systolic pressure, diastolic pressure, mean pressure and heart rate, the programming options for the disclosed circuitry can be utilized to generate and compute yet further data such as the pressure pulse product.

Digital display console 92 includes three main circuit sections (see FIG. 10), including analog section 104, microprocessor section 105 and digital display section 106, and each of these sections will be described hereinafter. Analog section 104 (see FIG. 9) includes three circuit subsections 104a, 104b and 104c, two of which, 104a and 104b, derive their output signals from pressure transducer device 90 inputs and the third of the three (104c) generates a Korotkoff pulse from piezoelectric crystal apparatus 41. Pressure transducer device 90 may be, for example, a model LX1602G offered by National Semiconductor Corporation of Santa Clara, Calif. The output of pressure transducer device 90 is coupled to a unity gain amplifier 107 and the output of amplifier 107 is applied to a unity gain inverting amplifier 108 which inverts the pressure voltage so that the output voltage will increase in proportion to increasing pressure. The output voltage scale factor is approximately 12.9 mV per 1 millimeter of mercury pressure. The D.C. pressure voltage output of amplifier 107 is also applied to circuit subsection 104b and is input to an A.C. coupled amplifier 109. An A.C. signal is superimposed on this D.C. pressure voltage input to amplifier 109 and amplifier 109 has a gain of approximately 50. The output of amplifier 109 is filtered by a second-order low pass filter 110 which passes only frequencies below approximately 20 HZ. The resultant output of filter 110 is amplified again by amplifier 111, which has a gain of approximately 20, and the output of amplifier 111 is compared by comparator 112 with a preset threshold voltage. When the input signal from amplifier 111 is larger than the preset threshold level, a logic level at the output of comparator 112 indicates the presence of a pressure wave which is the result of artery expansion as the patient's heart beats.

Figure 9:
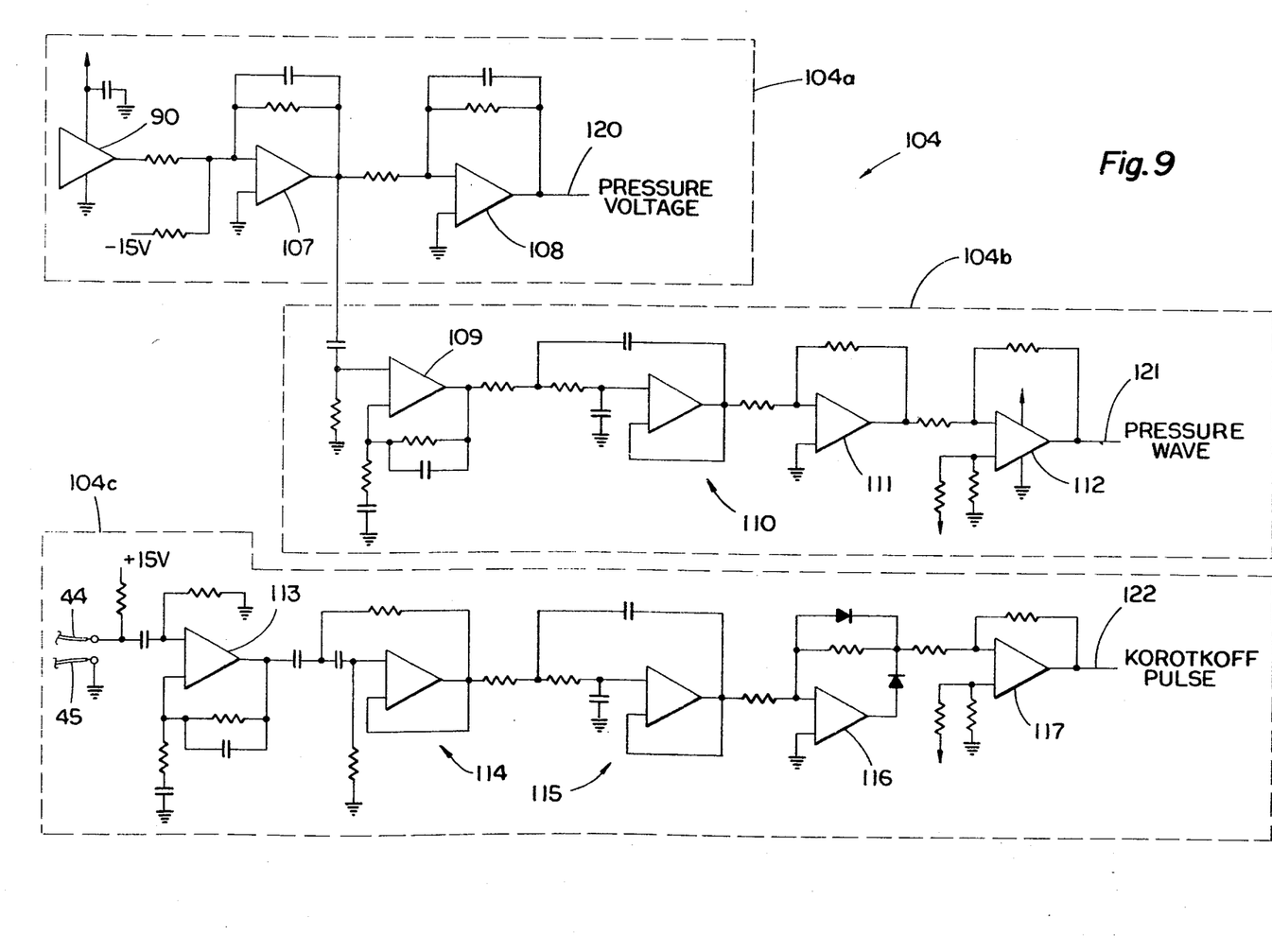
FIG. 9 is a schematic diagram of circuit subsections comprising a portion of the FIG. 7 device.

The final circuit subsection 104c is employed to detect the presence of Korotkoff pulses (frequency range 40-160 HZ) and piezoelectric crystal apparatus 41, by means of wires 44 and 45, provides the input signal to subsection 104c. A high impedance input amplifier 113, which has a gain of approximately 50, buffers the input, and the output of amplifier 113 is coupled to a second-order high pass filter 114 which removes frequencies below 40 HZ. Next is a second-order low pass filter 115, which removes those frequencies from the signal which are above 160 HZ, and the output of filter 115 is coupled to an absolute amplifier 116 having a gain of approximately 10. The final portion of circuit subsection 104c is a comparator 117 which compares the output signal of amplifier 116 with a preset threshold level, and if the output signal of amplifier 116 is larger than the threshold level, a logic signal to the output of comparator 117 will indicate the presence of a Korotkoff pulse. The application of the three circuit subsection outputs 120, 121 and 122 which may be present from analog section 104 will be understood by a review of FIG. 10 which illustrates in block diagram form the main circuitry blocks of blood pressure measuring device 89. Output 120 of circuit subsection 104a couples to a digital-to-analogconverter section 123a and in turn to Input/Output (I/O) devices 124, which is one of the main circuit sections of microprocessor section 105. Converter section 123a includes a converter 123 which may be, for example, a model AD561 offered by Analog Devices of Norwood, Mass. The other two outputs 121 and 122 couple directly to I/O devices 124. The remaining inputs to the I/O devices are from redisplay button 99 and ON/OFF switch 100. Microprocessor section 105 also includes a programmable read-only-memory 126 and a microprocessor 125. A suitable microprocessor for this application is an MCS 6502 offered by MOS Technology, Inc. of Norristown, Pa.; and a suitable programmable read-only-memory is a model 2716 EPROM offered by Intel Corporation of Santa Clara, Calif. The I/O devices 124 may be, for example, an MCS 6532 offered by MOS Technology, Inc. and includes within its capabilities a 128×8 static RAM and two software controlled 8 bit bi-directional data ports which allow direct interfacing between the microprocessor 125 and peripheral devices such as the twelve seven-segment digital display units 127 of digital display section 106. Start switch 98 couples directly to microprocessor 125 and a clock 128 provides the necessary timing control for device 89. The programmable read-only-memory 126 stores the software program which directs the microprocessor section 105, and the I/O devices 124 are selected based upon the particular problem to be solved.

Figure 10:
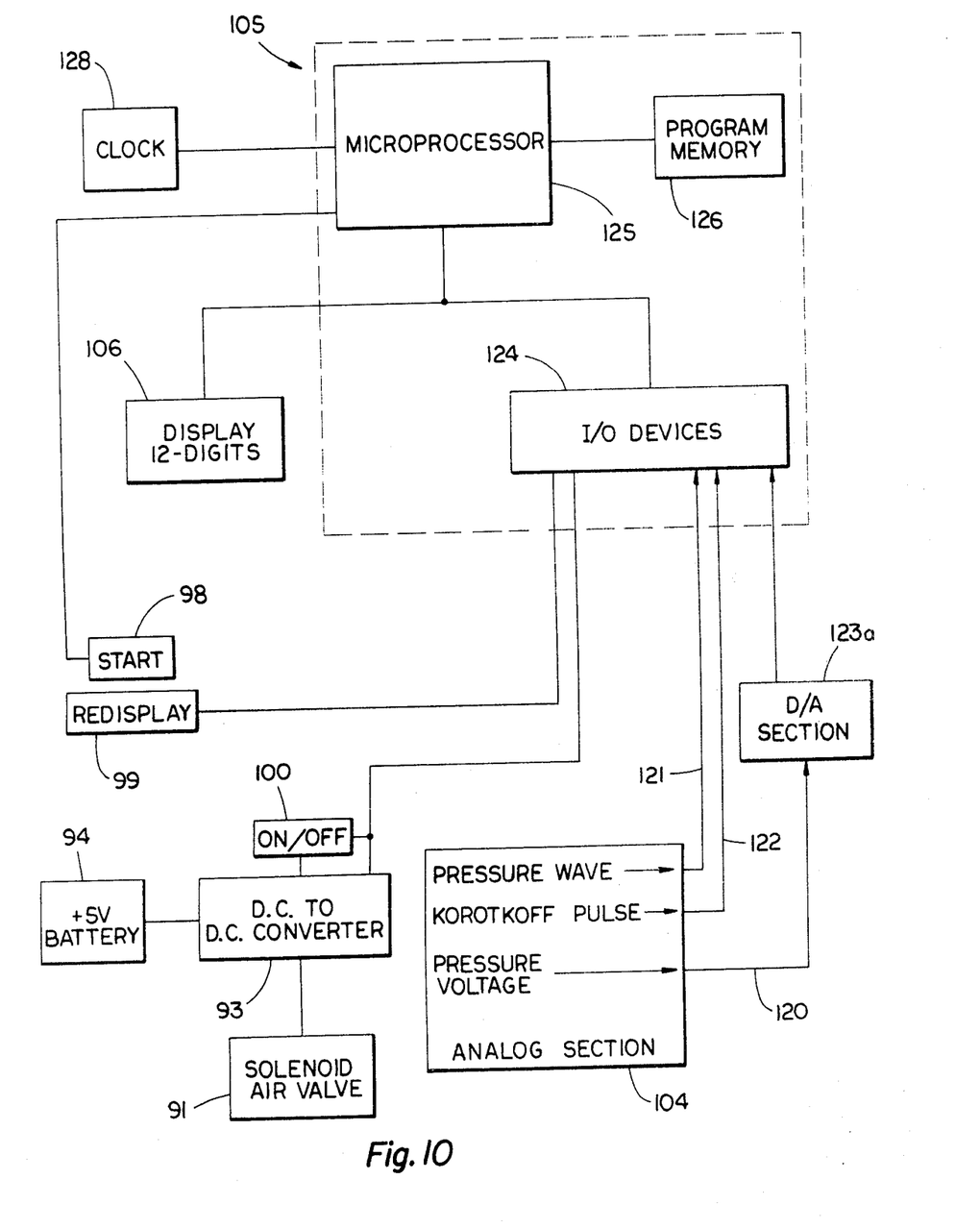
FIG. 10 is a block diagram of the circuitry of the FIG. 8 console.

The particular microprocessor software for device 89 operates device 89 in the following manner. ON/OFF switch 100, when placed in the ON position, will initialize device 89 by placing the various components and circuit sections in a ready condition. When the start switch is pressed, the D.C. to D.C. converter 93 is turned on and the compression cuff 21 connected to the inflation bulb by way of solenoid air valve 91. Pressure transducer 90 produces a signal representative of the pressure level within cuff 21 and this level is displayed in display window group 96. At this point, bulb 28 will be used to inflate cuff 21 to an artery occluding pressure level which, by definition, is above the systolic blood pressure level of the particular patient. However, the necessary artery occluding pressure level may not be known and so device 89 is provided with indicator means for signaling the user of device 89 if the pressure to which cuff 21 is initial inflated is not high enough to exceed the systolic pressure of the particular patient. The indicator means includes circuitry to cause the digits in the systolic pressure display window group 96 to blink on and off. When this blinking occurs, the user of device 89 merely needs to pump up cuff 21 to a higher pressure level by means of bulb 28. Once a pressure greater than systolic has been reached the device performs automatically. Display window group 96 continues to change its reading as the cuff pressure automatically deflates, due to air leak valve 30, at a rate of 2-3 mm of Hg. per second, until the detection of the first Korotkoff pulse. At this point, output 122 will signal I/O devices 124 that a pressure pulse has been received by piezoelectric crystal apparatus 41 due to the first flow of blood past the point along the artery which is now only partially occluded. As previously described, this passage of blood causes a slight expansion to cuff 21 which generates a pressure pulse and triggers piezoelectric crystal apparatus 41 into generating an electrical signal. The logic signal on output 122 causes the digits currently displayed in display window group 96, and which present systolic blood pressure, to be permanently held there until the device is turned off or reset for another measurement. As the cuff pressure continues to be released, the diastolic pressure display window group 96a displays the actual cuff pressure. However, when the artery is completely open and the blood flow is unimpeded through the artery at the point of the compression cuff, there will be no pressure pulses received by piezoelectric crystal apparatus 41 and thus no output signal will be generated. At this cessation of the Korotkoff pulses, the diastolic blood pressure which is displayed in display window group 96a will be held there until the device is turned off or reset for another measurement. As previously explained, the mean pressure may be computed and displayed in window group 96b once the systolic and diastolic pressures have been determined. The heart rate is derived from a 15 second count of the number of pressure wave pulses, caused by heart beats, which are received from the pressure transducer device 90 via circuit subsection 104b. When the heart rate is determined, the air in the cuff is released (via solenoid air valve 91) and the D.C. to D.C. converter 93 is turned off. There is an automatic turn off provision for device 89 which will turn off all four display windows approximately one minute after the heart rate has been obtained. Test results will be retained by I/O devices 124 until the start of a new cycle. However, redisplay button 99 permits a display window recall of the four numerical values previously visible. Also included as part of device 89 as an additional feature is a low power indicator for battery 94. As the battery becomes discharged, the displays of the unit will blink a warning to the user when device 89 is first turned on. Although it is possible to use device 89 in this particular condition, such use will be limited to only a few measurement cycles before the battery power level will be inadequate for further operation of device 89. Therefore battery replacement or battery recharging can be done conveniently during a non-use time.

Digital display section 106 consists of twelve seven-segment numerical display units 127 which may be driven by two model NE 590 addressable peripheral drivers offered by Signetics Corporation of Sunnyvale, Calif. Each driver has eight outputs which are turned on or off by respective loading of a logic high or a logic low into the device data input. The twelve displays are time multiplexed in order to reduce power consumption and interfacing circuitry requirements. This is accomplished by sequentially energizing each display, one at a time, at a cycle rate sufficiently fast so that all twelve displays will appear to be simultaneously illuminated.

Figure 11:
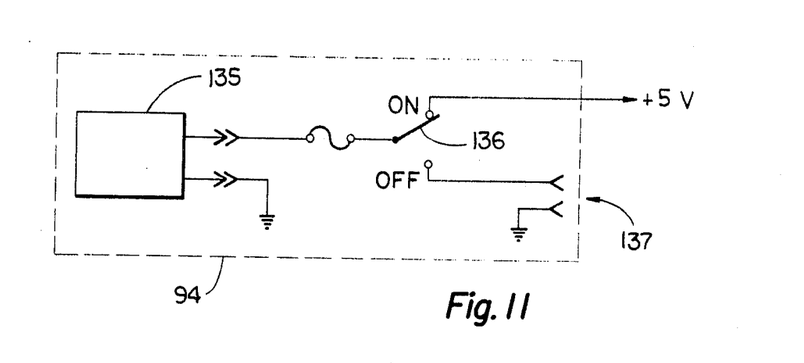
FIGS. 11 through 11e are detailed schematics corresponding to portions of the FIG. 10 block diagram.
Figure 11A:
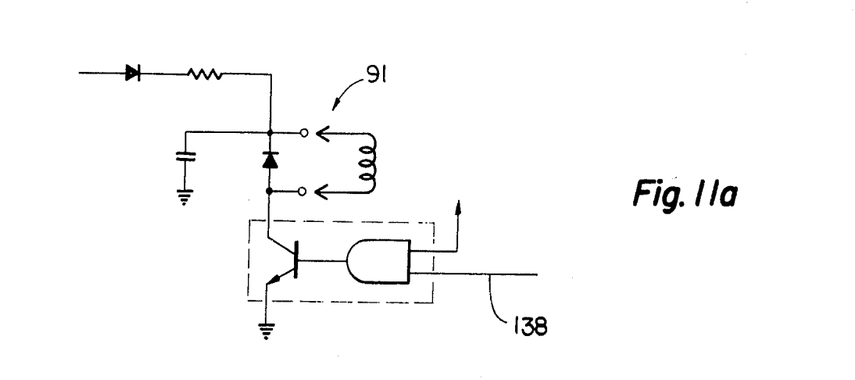
Figure 11B:
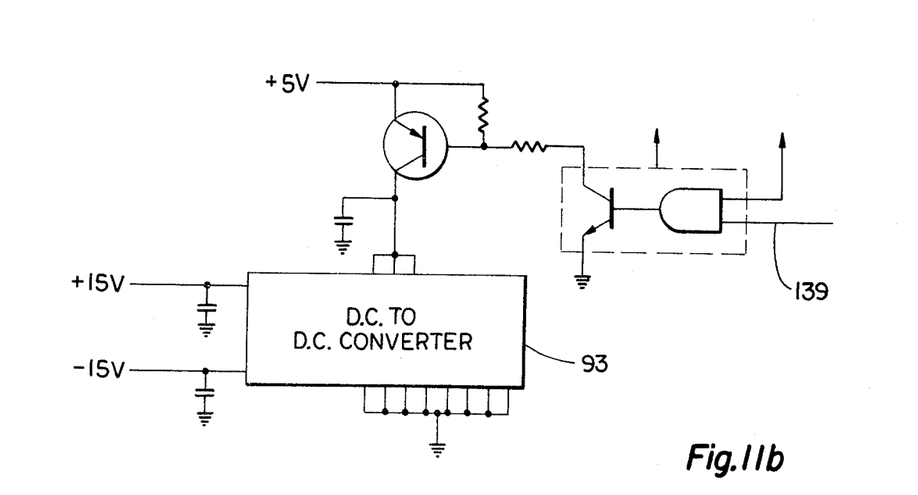
Figure 11C:
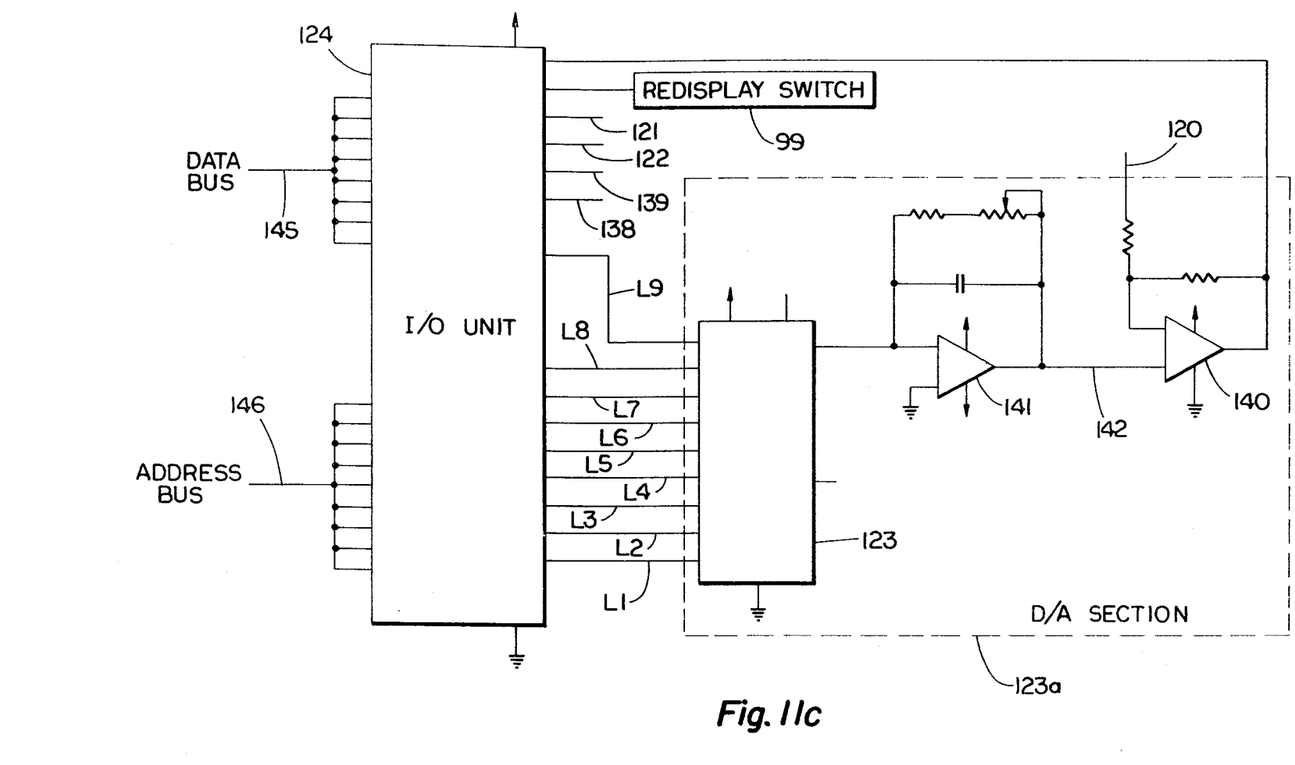
Figure 11D:
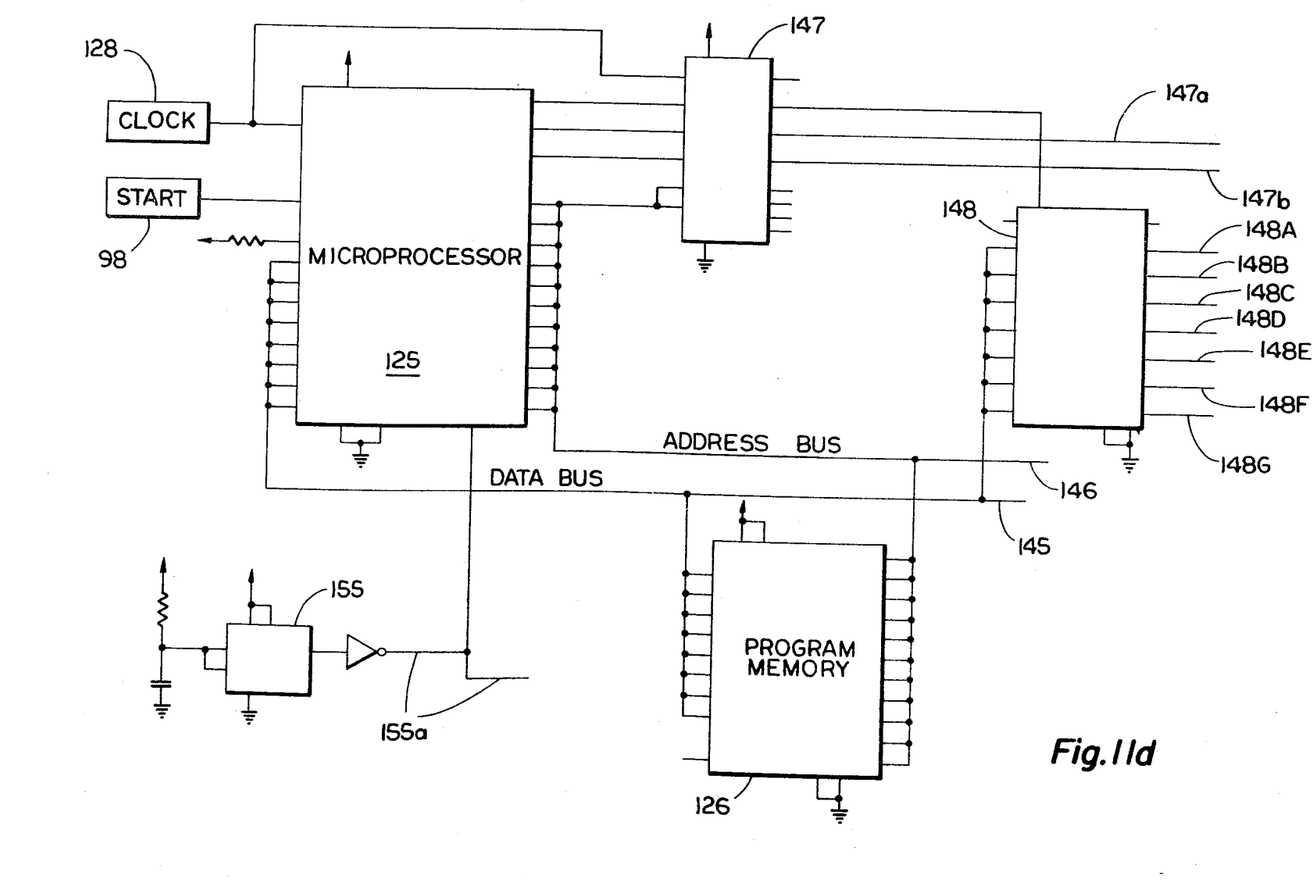
Figure 11E:
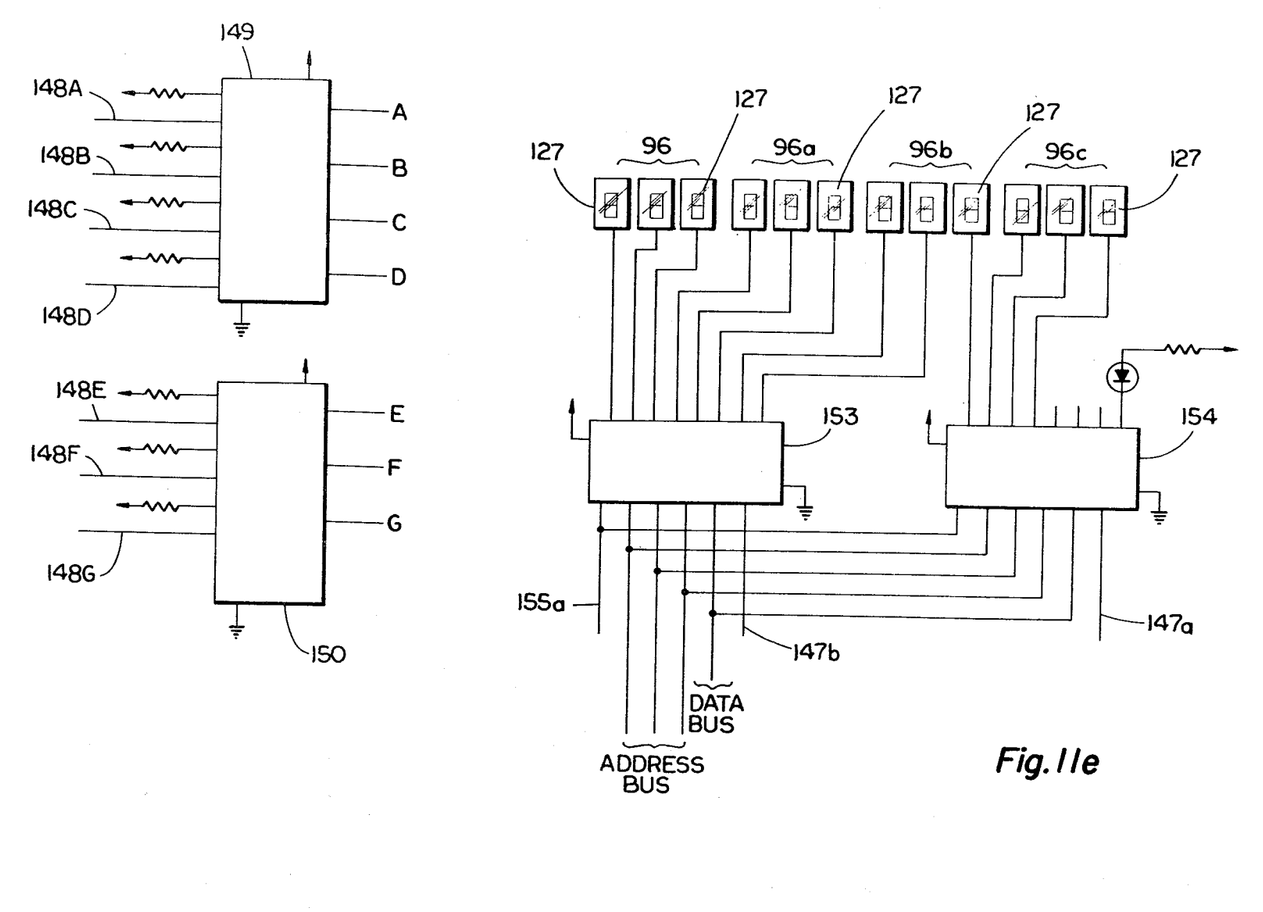

Referring to FIGS. 11-11e detailed circuitry is illustrated which corresponds to some of the circuit blocks of FIG. 10. Battery 94 includes a replaceable or rechargeable battery pack 135 and an ON-OFF switch 136 for switching the battery pack to power the unit or to the battery recharging plug 137. Recharging may be done via recharging input 101 (see FIG. 8). The circuitry associated with solenoid air valve 91 is illustrated by FIG. 11a and line 138 will carry a logical "1" when the solenoid is de-energized and a logical "0" when the solenoid is energized. The circuitry associated with D.C. to D.C. converter 93 is illustrated by FIG. 11b, wherein the plus 5 volt signal received from battery 94 is converted into both a plus and a minus 15 volt output. Line 139 carries a logical "1" when the converter is off and a logical "0" when the converter is on.

Referring to FIG. 11c, the pressure voltage signal on line 120 is input to the plus input of comparator 140 while the negative input of comparator 140 receives a preselected voltage level from converter 123 by way of amplifier 141. When the voltage on 120 is greater than the threshold level on line 142, an output signal will be conducted to I/O devices 124. Additional inputs to I/O devices 124 include those signals on output lines 121, 122, 138 and 139 as well as the line coupling to redisplay button 99. There is also additional data communication between convertor 123 and I/O devices 124 across lines L1 through L9 and a plurality of I/O devices outputs comprise data bus 145 and address bus 146. These bus lines are continued on as part of FIG. 11d and are coupled to programmable read-only-memory 126 and to microprocessor 125 as illustrated. Microprocessor 125 also receives inputs from clock 128 and start switch 98 and outputs from microprocessor 125 are coupled to address decoder 147 which may be, for example, an SN74LS138 offered by Texas Instruments, Incorporated of Dallas, Tex.

Included as part of the circuitry of digital display console 92 and illustrated in FIG. 11d is an eight-bit register 148 which generates the appropriate output signals on lines 148A through 148G, in response to the data stored in microprocessor 125, for illumination of the particular digital display 127 which is correspondingly enabled at the particular instant of time. Register 148 may be, for example, an SN74LS374 offered by Texas Instruments, Incorporated. The seven output lines of register 148 couple to display segments 149 and 150 which in turn selectively energize the appropriate segments of the seven-segment display 127 which is enabled. Addressable peripheral drivers 153 and 154 sequentially enable the twelve seven-segment digital displays 127 one at a time in a time multiplexed fashion such that each display is illuminated for approximately ten milliseconds out of each scan cycle. The data for determination of what digits should appear in each of twelve displays is stored within the microprocessor and is called forth in a time synchronous fashion as each one of the twelve digital displays 127 is sequentially multiplexed. Therefore, the output signals from address decoder 147 and eight-bit register 148 will change as first systolic pressure then diastolic pressure, and next mean pressure and finally heart rate are determined and displayed.

Also included as a part of the FIG. 11d circuitry is a timer 155 and its associated circuitry. Timer 155 may be, for example, an NE 555 offered by Signetics Corporation of Sunnyvale, Calif., and it is used to reset the system when power is first applied. Output line 155a couples to microprocessor 125 and addressable peripheral drives 153 and 154.

Although not all the active and passive components have been shown, the important concept is that pressure and pressure change data, as provided by analog section 104, are used by the programmable microprocessor circuitry in order to determine and display data which is characteristic of the blood circulation system of a particular animal, infant and/or adult. Inasmuch as commercially available components are utilized as part of digital display console 92, the particular interconnections from component to component, in excess of those illustrated by the various drawings, are well known in the microprocessor art. It is to be noted, however, that the particular design of the circuitry disclosed herein, and the specific arrangement of the selected components, provides a number of operational benefits which contribute to the reliability and ease of operation of device 89. Following is a flow chart type of discussion associated with device 89 which sets forth certain of these operational benefits.

As previously mentioned, placing ON/OFF switch 100 in the ON position initializes the entire system and sets the various components in a ready mode. Upon activating the start switch 98, converter 93 is turned on, solenoid air valve 91 connects the cuff 21 to the bulb 28 and window group 96 displays the existing cuff pressure. As the cuff is inflated the pressue in the cuff is displayed in window group 96, but it is not known whether or not a particular pressure level is above systolic, although the user of device 89 will rapidly inflate cuff 21 to a pressure which is assumed to be above the systolic pressure level. Due to the fact that the systolic pressure level of a particular patient or subject on whom device 89 is being used is not known, the device will sense when inflation has stopped by detecting a one second interval of cuff deflation; then, if two heart beats are received without the presence of a Kororkoff pulse, the device will proceed with the determination of the systolic blood pressure. However, if a Kororkoff pulse appears during the time of these first two heart beats then the systolic display, window group 96, will begin to blink and the user will need to inflate the cuff to a higher pressure level before continuing with the determination of the systolic blood pressure. Device 89 continues to monitor the pressure parameters from crystal apparatus 41 and pressure transducer 90 until a Kororkoff pulse is detected, at which time the pressure level in the cuff which has been displayed all along in window group 96 will be fixed and held in window group 96. The program control of device 89 then places the circuitry in a slightly different monitoring state. Now the I/O devices 124 and microprocessor 125 monitor the inputs for the absence of the Kororkoff pulses, and when no further Kororkoff sounds are being received, the pressure level in cuff 21 at that instant of time is held and displayed in window group 96a as the diastolic blood pressure. It is to be noted that window group 96a continuously displays the existing pressure in cuff 21 between the time that systolic pressure has been fixed and the time that the diastolic blood pressure is determined. Finally the mean pressure is computed and displayed in window group 96b and the heart rate is determined and displayed window group 96c. At this time, the converter 93 is turned off and solenoid 91 is de-energized, thereby dumping the pressure in cuff 21. The device then holds the four numerical values in the display windows for a time interval of approximately one minute, and at any time after that one minute interval, a new one minute interval can be initiated by depressing the redisplay button 99. Device 89 is unique in that cuff pressure is accurately monitored and displayed on a real time basis such that at the first instant a Kororkoff pulse is detected the circuitry isolates the number in the display and holds it there as an accurate representation of the systolic blood pressure of the particular subject. The fully automatic nature of device 89, wherein once the cuff is inflated to a pressure level above systolic the remainder of the procedure proceeds without user intervention, provides a quickness and accuracy in the determination of systolic and diastolic blood pressures which is unparalleled. Further safeguards are provided by the fact the I/O devices 124 and microprocessor 125 monitor both the heart beat pulses as well as the Kororkoff pulses, and it is known that these two signals must occur simultaneously. Therefore, extraneous signals which might not be true Kororkoff pulses can be detected and filtered out because they will not occur in synchronization with the heart beat pulses.

Although compression cuff 21 has been illustrated and described as a single member with a single inflatable bladder 22 inside which extends for substantially the full length of cuff 21, other cuff designs are possible without affecting the novelty and improvements disclosed herein. For example, a dual cuff design having an inflatable bladder on the proximal side and a permanently filled bladder on the distal side may be used. Such a dual cuff design is typical of that associated with an oscillometer and when the dual cuff is used with device 20 or device 89, the piezoelectric crystal apparatus 41 would be coupled to the filled bladder, distal side.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A blood pressure measuring device for identifying the pressure of a subject's blood at systolic and diastolic conditions which comprises:
   aneroid manometer means for indicating blood pressure measurements;
   a compression cuff having an inflatable bladder therein;
   a first length of flexible tubing flow coupled to said inflatable bladder;

a second length of flexible tubing flow coupled to said aneroid manometer means; and a quick disconnect bleed valve disposed coaxially with and between said first length of flexible tubing and said second length of flexible tubing and being arranged with tube connection means at each end.

2. The measuring device of claim 1 wherein said aneroid manometer means includes an externally visible dial face.

3. The measuring device of claim 2 wherein said aneroid manometer means includes indicator means for identifying the points in time at which to read said visible dial face for obtaining the subjects blood pressure at systolic and diastolic conditions.

4. The measuring device of claim 3 in which said indicator means includes at least one light-emitting diode positioned adjacent said dial face and an electronic circuit.

5. The measuring device of claim 4 which further includes an electronic circuit designed such that at said systolic condition said light-emitting diode turns on and at said diastolic condition said light-emitting diode turns off and said light-emitting diode alternately turns on and off with each heart beat between said systolic and diastolic conditions.

6. The measuring device of claim 5 in which said electronic circuit further includes a dual operational amplifier, the first stage of which being used for filtering and amplifying and the second stage of which being used as an comparator-timing circuit.

7. A method of determining blood circulation system characteristics which comprises:
   wrapping an inflatable bladder completely around a selected artery-containing appendage;
   turning on a remotely positioned electronic circuit which contains a pressure-sensitive piezoelectric crystal, said piezoelectric crystal being coupled to said inflatable bladder by a two-piece arrangement of tubing;
   inflating said bladder to a pressure level above the assumed systolic blood pressure of said blood circulation system; and
   allowing a bleed valve having a continuously open aperture to control the rate of deflation of said bladder, said bleed valve providing the juncture between said two pieces of tubing.

8. The method of claim 7 which comprises the following additional steps:
   watching at least one light-emitting diode, said diode comprising a portion of said circuit;
   reading a sphygmomanometer dial when said light-emitting diode first illuminates; and
   reading said dial again when said diode turns off.

9. The method of claim 8 which further includes the step of waiting as pressure in said bladder escapes through a continuously open air leak valve at a predetermined leak rate immediately following said inflating step.

* * * * *